US009334524B2

(12) United States Patent
Gluschankof et al.

(10) Patent No.: US 9,334,524 B2
(45) Date of Patent: May 10, 2016

(54) METHODS FOR IMPROVING AND MANAGING NUCLEOSIDE REVERSE-TRANSCRIPTASE INHIBITION BASED TREATMENT

(75) Inventors: Pablo Gluschankof, Marseille (FR); Christele Perrin-East, Marseille (FR)

(73) Assignee: AMIKANA, BIOLOGICS, Marseille (FR)

( * ) Notice: Subject to any disclaimer, the term of this patent is extended or adjusted under 35 U.S.C. 154(b) by 42 days.

(21) Appl. No.: 14/118,267

(22) PCT Filed: May 16, 2012

(86) PCT No.: PCT/EP2012/002107

§ 371 (c)(1), (2), (4) Date: Jan. 31, 2014

(87) PCT Pub. No.: WO2012/156086

PCT Pub. Date: Nov. 22, 2012

(65) Prior Publication Data

US 2014/0141461 A1 May 22, 2014

(30) Foreign Application Priority Data

May 17, 2011 (EP) .................................... 11004055

(51) Int. Cl.

| | |
|---|---|
| ***C07H 19/06*** | (2006.01) |
| ***C07H 19/10*** | (2006.01) |
| ***C12Q 1/48*** | (2006.01) |
| ***C07K 14/705*** | (2006.01) |
| ***C12N 9/12*** | (2006.01) |
| ***C12N 9/88*** | (2006.01) |
| ***C12N 15/81*** | (2006.01) |

(52) U.S. Cl.

CPC .............. *C12Q 1/485* (2013.01); *C07K 14/705* (2013.01); *C12N 9/1205* (2013.01); *C12N 9/1276* (2013.01); *C12N 9/88* (2013.01); *C12N 15/81* (2013.01); *C12Y 207/01074* (2013.01); *C12Y 207/07049* (2013.01); *C12Y 402/01019* (2013.01)

(58) Field of Classification Search

CPC combination set(s) only.
See application file for complete search history.

(56) References Cited

PUBLICATIONS

Nissley et al (Sensitive Phenotypic detection of Minor Drug-resistant Human Immunodeficiency Virus Type 1 reverse Transcriptase Variants Journal of Clinical Microbiology).*
Huber-Rano et al (Transport of Nucleoside analogues across the plasma membrane: A clue to understanding drug induced cytotoxicity Current Drug Metabolism Science Publishers US vol. 10, No. 4, pp. 1389-2002 2005).*
Pastor-Anglda (Cell Entry and export of nucleoside analogues (Virus Research 107 (2005) 151-164.*
Visser et al (Residue 334 and 338 in transmembrane segment 8 of Human Equilibrative Nucleoside Transporter 1 Are important Determinants of Inhibitor sensitivity, Protein Folding, and Catalytic turnover (Journal of Biological Chemistry, vol. 282, No. 19, Mar. 22, 2007, pp. 14148-14157).*
Viggiani et al (New vectors for simplifies construction of BrdU-incorporating strains of *Saccharomyces cerevisiae* Yeast, vol. 23, np. 14-15, Jan. 1, 2006, p. 1045-1051).*

* cited by examiner

*Primary Examiner* — Kagnew H Gebreyesus
(74) *Attorney, Agent, or Firm* — Young & Thompson

(57) ABSTRACT

A transformed yeast cell includes: a nucleic acid sequence coding for a reverse transcriptase; a reverse transcription indicator; a nucleic acid sequence coding for deoxycytidine kinase (dCK); and at least one nucleic acid sequence coding for nucleoside transporter. Methods for screening a compound with the ability to inhibit reverse transcription and for predicting the sensitivity of a reverse transcriptase to a NRTI compound, particularly a reverse transcriptase derived from a virus infecting a subject using the transformed Yeast cell are also described.

6 Claims, 3 Drawing Sheets

METHODS FOR IMPROVING AND MANAGING NUCLEOSIDE REVERSE-TRANSCRIPTASE INHIBITION BASED TREATMENT

This patent application claims the priority benefit of European Patent Application EP11004055.7 filed May 17, 2011 which is incorporated herein by reference.

SEQUENCE LISTING

An attached Substitute Sequence Listing (i. Name: SEQCRF_0752-1050, ii. Date of Creation: Jan. 31, 2014, and iii. Size: 32 KB) is based on the Sequence Listing filed with U.S. application Ser. No. 14/118,267.

FIELD OF THE INVENTION

The present invention relates to cells and methods for detecting nucleoside reverse transcriptase inhibitors and for predicting the sensitivity of a reverse transcriptase to a nucleoside reverse transcriptase inhibitor (NRTI) treatment.

BACKGROUND OF THE INVENTION

Some viral infections constitute real health problems for the society. Among them, HIV (Human Immunodeficiency Virus) infection is one of the most serious diseases affecting humankind. The development of new therapeutic strategies, such as combination of chemotherapy, has really improved the quality and the expectancy of life of patients infected by HIV. There are different classes of anti-HIV drugs, including anti-reverse transcriptase compounds, anti-integrase compounds, anti-entry compounds and anti-protease compounds. The reverse transcriptase inhibitors include nucleoside reverse transcriptase inhibitors (NRTI) and non nucleoside reverse transcriptase inhibitors (NNRTI).

Unfortunately, in response to these drugs, the virus mutes, and drug resistances appear, leading to treatment failure. Thus, viral drug resistance and sensitivity are important subject matters for scientists working on the improvement of therapeutic strategies and there is an important need for studying such mechanisms, for identifying new antiviral drugs and for managing antiviral treatments.

The reverse transcriptase of HIV is subjected to mutations, leading to resistances against reverse transcriptase inhibitors. Several tests have been developed for detecting new reverse transcriptase inhibitors. The U.S. Pat. Nos. 5,714,313 and 5,462,873 describe a simple and non expensive test for detecting reverse transcriptase inhibitors in a yeast cell. However, and even if this method can be used for non nucleoside reverse transcriptase inhibitors (NNRTI), such a test is not adapted for detection of nucleoside reverse transcriptase inhibitors (NRTI). Indeed, NRTI are prodrugs which have to enter into the cell through nucleoside transporters and which have to be tri-phosphorylated by cellular kinases to be efficient; the yeast genome is devoid of the necessary genetic information for the transporters and kinases involved in the production of mono-phosphorylated nucleosides.

Thus, there is a need to adapt the test described in the U.S. Pat. Nos. 5,714,313 and 5,462,873, in order to test NRTI or candidate NRTI compounds.

SUMMARY OF THE INVENTION

The inventors have now developed a transformed yeast cell, wherein the specific expression of deoxycytidine kinase (dCK) and of at least one nucleoside transporter enables the nucleoside reverse transcriptase inhibitors (NRTI) to be functional into said transformed yeast cell.

The invention relates to a transformed yeast cell comprising:

- a nucleic acid sequence coding for a reverse transcriptase,
- a reverse transcription indicator,
- a nucleic acid sequence coding for a deoxycytidine kinase (dCK), and
- at least one nucleic acid sequence coding for a nucleoside transporter.

Said transformed yeast cell enables to test the activity of nucleoside reverse transcriptase inhibitors (NRTI) on said reverse transcriptase.

The invention also relates to a method for screening a compound with the ability to inhibit reverse transcription comprising the steps of:

i. contacting a transformed yeast cell containing a reverse transcriptase indicator according to the invention with a compound,
ii. culturing said transformed yeast cell in a selective medium,
iii. detecting inhibition of growth of the transformed yeast cell compared to said transformed yeast cell that is not contacted with said compound, and
iv. selecting a compound with the ability to inhibit growth of the transformed yeast cell as being a compound that inhibit reverse transcription.

The invention also relates to a method for predicting the sensitivity of a reverse transcriptase to a NRTI compound, said method comprising the steps of:

i. producing a transformed yeast cell as previously described, comprising the reverse transcriptase to be studied,
ii. contacting said transformed yeast cell with said NRTI compound,
iii. culturing the transformed yeast cell in a selective medium,
iv. determining the growth of the transformed yeast cell with or without NRTI compound, and
v. deducing therefrom if the reverse transcriptase to be studied is sensitive or resistant to said NRTI treatment.

BRIEF DESCRIPTION OF THE DRAWINGS

The drawings form part of the present specification and are included to further demonstrate certain aspects of the present invention. The invention may be better understood by reference to one or more of these drawings in combination with the detailed description of specific embodiments presented herein.

DETAILED DESCRIPTION OF THE INVENTION

Figure 1:
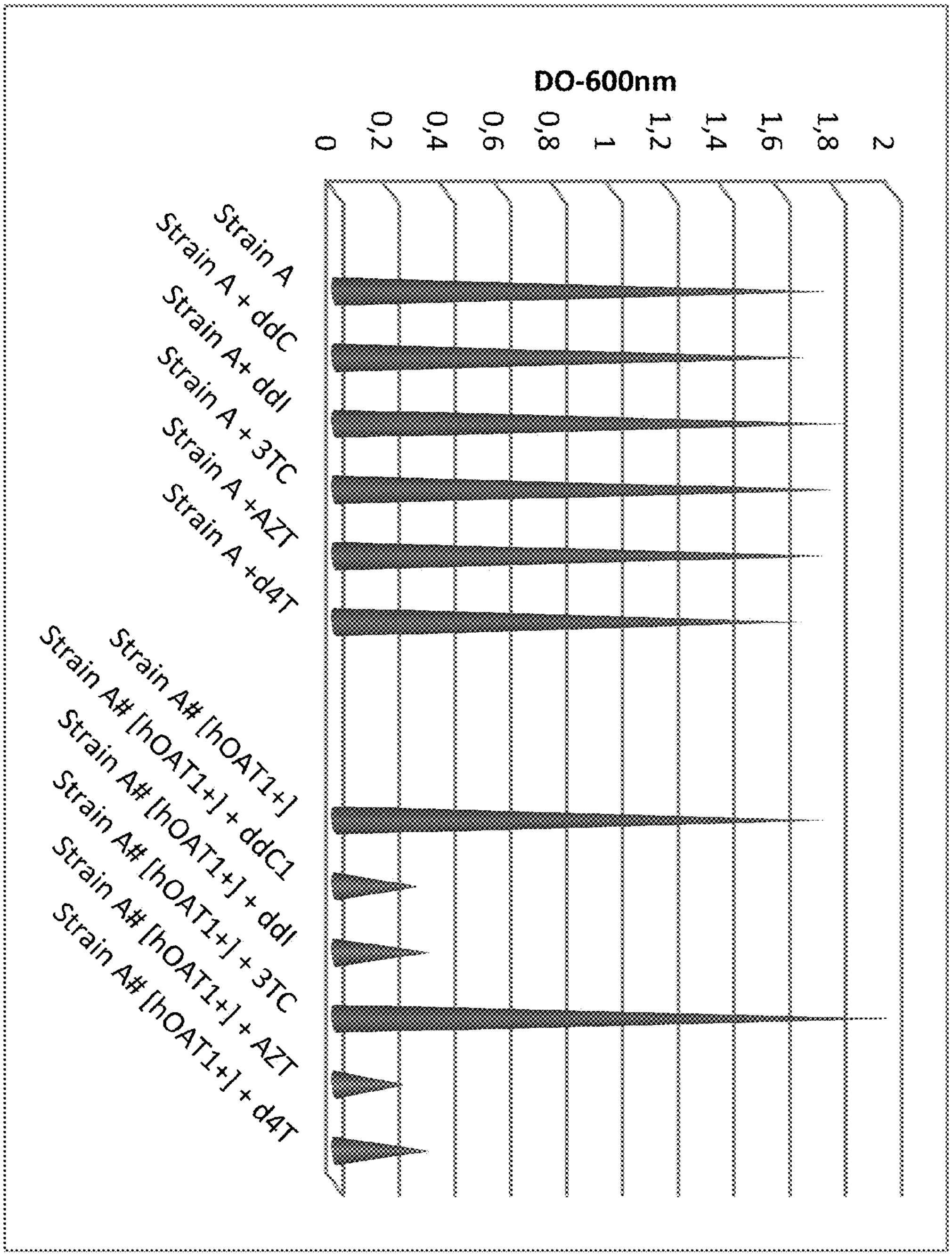
FIG. 1: Reverse transcriptase (RT) activity and inhibitor susceptibility in strain carrying dCK in its genome and OAT1 in a plasmid. The FIG. 1 shows that when the reverse transcriptase from HIV-1 is expressed as described in U.S. Pat. No. 5,714,313, in yeast Strain A (Mat a, URA−, HIS−, LEU−) (thus not carrying dCK and OAT1), incubation for 72 hours in the presence of either Zalcitabine (ddC) (Strain A+ddc 100 μM), Didanosine (ddI) (Strain A+ddI 100 μM), Zalcitabine (AZT) (Strain A+AZT 100 μM) or Stavudine (d4T) (Strain A+d4T 100 μM), can not inhibit cell growth, then reverse transcription, measured by absorbance at 600 nm (OD @ 600 nm). When the reverse transcriptase from HIV-1 is expressed as described in U.S. Pat. No. 5,714,313, in genetically modified Strain A that harbours a plasmid containing the nucleic acid sequence coding for the OAT1 transporter and where the dCK nucleic acid coding sequence was integrated in the yeast genome (Strain A#), incubation for 72 hours in the presence of either ddC (Strain A#+ddc 100 μM), ddI (Strain A#+ddI 100 μM), AZT (Strain A#+AZT 100 μM) or d4T (Strain A#+d4T 100 μM), inhibits cell growth, and then reverse transcription, measured by absorbance at 600 nm (OD @ 600 nm).

Thus, the inventors have developed and tested new constructions and yeast cells useful for detecting and testing NRTI compounds in system derived from the method described in the U.S. Pat. Nos. 5,714,313 and 5,462,873, which are incorporated herein by reference.

Yeast Cells of the Invention

A first object of the invention relates to a transformed yeast cell comprising:

- a nucleic acid sequence coding for a reverse transcriptase,
- a reverse transcription indicator,
- a nucleic acid sequence coding for a deoxycytidine kinase (dCK), and
- at least one nucleic acid sequence coding for a nucleoside transporter.

These elements may be comprised in the genome or in plasmids.

In a preferred embodiment, the invention relates to a transformed yeast cell comprising:

- a nucleic acid sequence coding for a reverse transcriptase and a reverse transcription indicator in a plasmid, and
- a nucleic acid sequence coding for a deoxycytidine kinase (dCK) and at least one nucleic acid sequence coding for a nucleoside transporter in its genome.

Said transformed yeast cell enables to test the activity of nucleoside reverse transcriptase inhibitors (NRTI) on said reverse transcriptase.

The term "NRTI" or "nucleoside reverse transcriptase inhibitor" refers to a nucleoside analog used as an antiretroviral drug whose chemical structure constitutes a modified version of a natural nucleoside. Such compounds suppress replication of retroviruses by interfering with the retroviral reverse transcriptase by taking the place of physiological nucleosides in the viral retro transcription event leading to random arrest of the viral nascent DNA. They can also be used for inhibiting all form of reverse transcriptase, particularly non retroviral reverse transcriptase.

The NRTI group encompasses, but is not limited to, Zidovudine (also called AZT, RETROVIR), Didanosine (also called ddI, VIDEX), Zalcitabine (also called ddC, HIVID), Stavudine (also called d4T, ZERIT), Lamivudine (also called 3TC, EPIVIR), Abacavir (also called ABC, ZIAGEN), Emtricitabine (also called FTC, EMTRIVA), Tenofovir (also called TFV VIREAD), Entecavir (BARACLUDE), Apricitabine (phase III clinical trial).

By "transformed yeast cell" is meant a yeast cell into which a vector (or a DNA fragment) of interest is transferred by any means, such as by infection, conjugation, transformation, electroporation, microinjection. Methods of cell transformation are well known in the art.

In one embodiment, the transformed yeast cell of the invention is a *Saccharomyces cerevisiae* transformed cell.

As used herein, a "reverse transcriptase" refers to a protein which has several activities, including a RNA-dependent DNA polymerase activity, and/or a RNase H activity and/or a DNA-dependent DNA polymerase activity; preferably at least a RNA-dependent DNA polymerase activity. A "reverse transcriptase" as used herein includes a reverse transcriptase derived from any virus, more particularly from any retrovirus or from any retrotransposon, as well as such reverse transcriptase variants harboring mutations and keeping the reverse transcriptase activities cited above.

As used herein, a "variant" or a "function-conservative variant" includes a nucleic acid sequence in which one or several nucleotides have been changed and which has at least 80% nucleotide identity as determined by BLAST or FASTA algorithms, preferably at least 90%, most preferably at least 95%, and even more preferably at least 99%, and which has the same or substantially similar properties or functions as the native or parent gene to which it is compared.

According to the invention, the reverse transcriptase used in said method is particularly a retroviral reverse transcriptase.

The reverse transcriptase used in the present invention may be for example derived from human immunodeficiency viruses HIV-1 and HIV-2, simian immunodeficiency virus, avian immunodeficiency virus, bovine immunodeficiency virus, feline immunodeficiency virus or equine infectious anemic virus. Preferably, the reverse transcriptase of the invention is a HIV-1 or HIV-2 reverse transcriptase.

According to the invention, the nucleic acid coding for a reverse transcriptase may be manufactured or obtained from a subject sample, said subject being infected by a virus of interest expressing a reverse transcriptase or more particularly a retrovirus of interest.

As used herein, the term "subject" denotes an animal infected by a virus, particularly a retrovirus, more particularly a mammal infected by a retrovirus, such as a rodent, a feline, a canine, and a primate. Preferably, a subject according to the invention is a human. More preferably, the subject is a human patient infected by HIV-1 or HIV-2.

A nucleic acid sequence coding for a reverse transcriptase obtained from a subject may be obtained by gene amplification (Polymerase Chain Reaction technique, PCR) or by release of the reverse transcriptase by virtue of action of restriction enzymes on purified viral DNA. For this, a biological sample containing the retrovirus genome information is obtained from the subject. For example, if the subject is a human patient infected by the HIV-1 or HIV-2 virus, the nucleic acid sequence coding for HIV-1 or HIV-2 reverse transcriptase may be obtained from the lymphocytes or plasma of a whole blood sample obtained from said patient, or from any other infected organ. Such methods are well known in the art (See for example, the methods disclosed in DWIGHT et al., Journal of Clinical Microbiology 2005, vol 43, n11, pp 5696-5704; and in SHAFER et al., Journal of Clinical Microbiology 1996, vol 34, n7, pp 1849-1853).

A nucleic acid sequence coding for a reference HIV-1 reverse transcriptase is defined by the nucleic acid sequence SEQ ID NO:1 A nucleic acid sequence coding for a reference HIV-2 reverse transcriptase is defined by the nucleic acid sequence SEQ ID NO:2. These both HIV-1 and HIV-2 reference reverse transcriptase are sensitive to NRTI treatment.

On the basis of these nucleic acid sequences, a skilled person can simply design on the basis of its general knowledge primers able to amplify by PCR HIV-1 or HIV-2 reverse transcriptase nucleic acid sequences on DNA obtained from an infected patient sample.

As an example, the nucleic acid sequence coding for the HIV-1 or HIV-2 reverse transcriptase may be amplified by PCR from a blood sample of an infected patient using the pair of primers defined by the nucleic acid sequences SEQ ID NO:3 and SEQ ID NO:4 or the pair of primers defined by the nucleic acid sequences SEQ ID NO:5 and SEQ ID NO:6.

In a preferred embodiment, the nucleic acid sequence coding for a reverse transcriptase is under the control of an inducible promoter.

The term "inducible promoter" refers to a transcriptional promoter that promotes transcription of appropriate genes when certain environmental conditions are present. Said promoter is efficient in the yeast cell of the invention. Examples of inducible promoters include, but are not limited to GAL-1 promoter which is inducible by galactose and ADH-2 which is inducible by glucose depletion and MET which is repressed by methionine.

The term "reverse transcription indicator" refers to a marker nucleic acid sequence which permits to check the integration, the expression and the functionality of a nucleic acid sequence coding for a reverse transcriptase inserted into a transformed cell of the invention, preferably in the genome (chromosomal DNA) of the transformed cell. In other terms, a "reverse transcription indicator" according to the invention indicates the presence of a reverse transcriptase activity. In a preferred embodiment, the reverse transcriptase indicator used for the invention is the his3AI gene, which is well known in the art and particularly described in U.S. Pat. Nos. 5,714,313 and 5,462,873.

The U.S. Pat. Nos. 5,714,313 and 5,462,873 describe a method for selecting the transformed yeast cells wherein retrotransposition has occurred, which can be used for the present invention. This method comprises the steps of (i) placing the transformed yeast cells onto a selective medium, (ii) culturing the cells, and (iii) selecting for growing colonies (colonies of the cells which grow).

As used herein, the term "deoxycytidine kinase (dCK)" refers to a polypeptide which transfers phosphate to deoxycytidine. dCK is required for the phosphorylation of several deoxyribonucleosides and their nucleoside analogs. The term may include naturally occurring dCK and variants and modified forms thereof. The dCK may be from any species, particularly a mammalian dCK, preferably a human dCK. An exemplary native human dCK mRNA sequence is provided in GenBank database under accession number NM_000788 (SEQ ID NO:7).

As used herein, the term "nucleoside transporter" refers to a large group of membrane transport proteins which transport nucleosides (and particularly nucleosides analogs) across the membranes of cells and/or vesicle. Nucleoside transporters particularly encompass, but are not limited to, equilibrate nucleoside transporters (ENT) and concentrate nucleoside transporters (CNT). According to the invention, the term also encompasses the organic anion transporters (OAT) and the organic cation transporters (OCT).

According to the invention, the nucleoside transporter may for example be selected in the group comprising, but not limited to, CNT1, CNT2, CNT3, ENT1, ENT2, OAT1, OAT3 and OCT1.

In a particular embodiment, the nucleoside transporter is selected in the group comprising, but not limited to, CNT1, CNT2, CNT3, ENT1, ENT2 and OAT1.

The term ENT1 for equilibrate nucleoside transporter 1 refers to a protein that in humans is encoded by the SLC29A1 gene. The term may include naturally occurring SLC29A1 gene and variants and modified forms thereof. The SLC29A1 gene is typically a mammalian SLC29A1 gene, preferably a human SLC29A1 gene. An exemplary native human SLC29A1 mRNA sequence is provided in GenBank database under accession number NM_001078174 (SEQ ID NO:8).

The term ENT2 (equilibrate nucleoside transporter 2) refers to a protein that in humans is encoded by the SLC29A2 gene. The term may include naturally occurring SLC29A2 gene and variants and modified forms thereof. The SLC29A2 gene is typically a mammalian SLC29A2 gene, preferably a human SLC29A2 gene. An exemplary native human SLC29A2 mRNA sequence is provided in GenBank database under accession number NM_001532 (SEQ ID NO:9).

The term CNT1 (concentrative nucleoside transporter 1) is a protein that in humans is encoded by the SLC28A1 gene. The term may include naturally occurring SLC28A1 gene and variants and modified forms thereof. The SLC28A1 gene is typically a mammalian SLC28A1 gene, preferably a human SLC28A1 gene. An exemplary native human SLC28A1 mRNA sequence is provided in GenBank database under accession number NM_004213 (SEQ ID NO:10).

The term CNT2 (concentrative nucleoside transporter 2) is a protein that in humans is encoded by the SLC28A2 gene. The term may include naturally occurring SLC28A2 gene and variants and modified forms thereof. The SLC28A2 gene is typically a mammalian SLC28A2 gene, preferably a human SLC28A2 gene. An exemplary native human SLC28A2 mRNA sequence is provided in GenBank database under accession number NM_004212 (SEQ ID NO:11).

The term CNT3 (concentrative nucleoside transporter 3) is a protein that in humans is encoded by the SLC28A3 gene. The term may include naturally occurring SLC28A3 gene and variants and modified forms thereof. The SLC28A3 gene is typically a mammalian SLC28A3 gene, preferably a human SLC28A3 gene. An exemplary native human SLC28A3 mRNA sequence is provided in GenBank database under accession number NM_001199633 (SEQ ID NO:12).

The term OAT1 (organic anion transporter 1) is a protein that in humans is encoded by SLC22A6 gene. The term may include naturally occurring SLC22A6 gene and variants and modified forms thereof. The SLC22A6 gene is typically a mammalian SLC22A6 gene, preferably a human SLC22A6 gene. An exemplary native human SLC22A6 mRNA sequence is provided in GenBank database under accession number NM_004790 (SEQ ID NO:13).

The term OATS (organic anion transporter 3) is a protein that in humans is encoded by SLC22A8 gene. The term may include naturally occurring SLC22A8 gene and variants and modified forms thereof. The SLC22A8 gene is typically a mammalian SLC22A8 gene, preferably a human SLC22A8 gene. An exemplary native human SLC22A8 mRNA sequence is provided in GenBank database under accession number NM_001184732 (SEQ ID NO:14).

The term OCT1 (organic cation transporter 1) is a protein that in humans is encoded by SLC22A1 gene. The term may include naturally occurring SLC22A1 gene and variants and modified forms thereof. The SLC22A1 gene is typically a mammalian SLC22A8 gene, preferably a human SLC22A1 gene. An exemplary native human SLC22A1 mRNA sequence is provided in GenBank database under accession number NM_003057 (SEQ ID NO:15).

According to the invention, the transformed yeast cell may comprise in its genome one, two, three, four, five, six, seven or eight nucleic acids sequences coding for nucleoside transporters.

In one embodiment of the invention, the transformed yeast cell of the invention at least comprises the nucleic acid sequence coding for OAT1.

In fact, the inventors have established that the expression of OAT1 enables to obtain a good inhibition of HIV RT by Zidovudine, Stavudine, Didanosine or Zalcitabine. In a particular embodiment, said transformed yeast cell at least comprises one more nucleic acid sequence coding for another nucleoside transporter.

In another embodiment of the invention, the transformed yeast cell of the invention at least comprises the nucleic acid sequence coding for CNT3.

In fact, the inventors have established that the expression of CNT3 enables to obtain a good inhibition of HIV RT by AZT (Zidovudine) or by d4T (Stavudine). In a particular embodiment, said transformed yeast cell at least comprises one more nucleic acid sequence coding for another nucleoside transporter.

In a particular embodiment of the invention, the transformed yeast cell of the invention further comprises a nucleic acid sequence coding for a thymidine kinase.

As used herein, the term "thymidine kinase" (TK) has its general meaning in the art and refers to a kinase (which is required for the action of many antiviral drugs). TK is required for the phosphorylation of several nucleoside analogs. The term may include naturally occurring TK and variants and modified forms thereof. The TK may be from any species. The TK may be for example a human TK, but also a viral TK. Typically, the TK used according to the invention may be the TK from Human Herpes Simplex Virus Type 1 HSV1-TK (SEQ ID NO:16).

Methods of the Invention

The transformed yeast cells of the invention may be used for improving and managing therapies using Nucleoside Reverse Transcriptase Inhibitors (NRTI).

Thus, a second object of the invention relates to a method for screening a compound with the ability to inhibit reverse transcription comprising the steps of:

i. contacting a transformed yeast cell containing a reverse transcription indicator according to the invention with a compound,
ii. culturing said transformed yeast cell in a selective medium,
iii. detecting inhibition of growth of the transformed yeast cell compared to said transformed yeast cell that is not contacted with said compound, and
iv. selecting a compound with the ability to inhibit growth of the transformed yeast cell as being a compound that inhibit reverse transcription.

According to the invention, the term "inhibition of growth" includes a significant decrease in growth compared to cells that are not contacted with the screened or tested compound. It thus includes any relative inhibition of growth that can be quantified.

In a particular embodiment, said inhibition of growth refers to a decrease of at least 30%, more particularly of at least 50%, even more particularly of at least 60%, preferably of at least 70%, more preferably of at least 80%, even more preferably of at least 90% in growth compared to cells that are not contacted with the screened or tested compound, wherein said compound is used at the higher concentration permitting its solubility in aqueous medium.

According to the invention, the reverse transcription indicator permits to the transformed yeast cell of the invention to grow in particular conditions in which non-transformed yeast cells (or transformed yeast cell in which reverse transcription does not occur) could not grow. The reverse transcription indicator thus enables selection of transformed yeast cells in which reverse transcription occurs, which are of interest for the invention.

The selective medium is chosen so as to select yeast cells able to grow in said particular conditions, in which reverse transcription effectively occurs.

For example, in the case of use of his3AI as reverse transcription indicator, yeast cells in which the reverse transcription occurs are able to grow in a medium lacking histidine. Thus, selective medium used with the his3AI gene as reverse transcription indicator is a medium lacking in histidine.

According to the invention, a transformed yeast cell of the invention which has been contacted with a tested NRTI compound grows in a classical cell culture medium (which is not selective).

For studying the effect of the tested NRTI compound on reverse transcription, said compound has to be added before the reverse transposition occurred.

So, preferably, the nucleic acid sequence coding for reverse transcriptase is under the control of an inducible promoter and reverse transcription (e.g. inducing the expression of the nucleic acid sequence encoding reverse transcriptase) is induced after contacting the tested NRTI compound with the transformed yeast cell of the invention.

Thus, in a preferred embodiment, the invention relates to a method for screening a compound with the ability to inhibit reverse transcription comprising the steps of:

i. contacting a transformed yeast cell containing a reverse transcription indicator and a reverse transcriptase under control of an inducible promoter according to the invention with a compound,
ii. inducing reverse transcription,
iii. culturing said transformed yeast cell in a selective medium,
iv. detecting inhibition of growth of the transformed yeast cell compared to said transformed yeast cell that is not contacted with said compound, and
v. selecting a compound with the ability to inhibit growth of the transformed yeast cell as being a compound that inhibit reverse transcription.

According to the method of the invention, compounds that could be tested according to the invention have a chemical structure similar to nucleosides and known NRTI.

According to the invention, the compounds selected according to this method can be used for developing therapeutic strategies against the retrovirus from which the reverse transcriptase of the transformed yeast cell is derived.

According to the invention, said reverse transcriptase may be from retrotransposons or viruses; particularly retroviruses.

Reverse transcriptases encoded in retrotransposon elements are implicated in cancer mechanisms and viral reverse transcriptases (more particularly retroviral reverse transcriptases) in viral infections.

In a particular embodiment, said reverse transcriptase may be from retroviruses.

In this case, the method of the invention permits to detect new compounds inhibiting retroviral replication.

According to the invention "inhibiting retroviral replication" can be used interchangeably with "inhibiting the reverse transcriptase" or "inhibiting reverse transcription" in the case of a retroviral reverse transcriptase.

In a more particular embodiment of the invention, the reverse transcriptase of the transformed cell used in this method is derived from a retrovirus selected in the group comprising HIV-1 and HIV-2, simian immunodeficiency virus, avian immunodeficiency virus, bovine immunodeficiency virus, feline immunodeficiency virus or equine infectious anemic virus. Preferably, the reverse transcriptase is derived from HIV-1 or HIV-2.

In another preferred embodiment, compounds selected by the methods of the invention may further be tested in a model of infection by the retrovirus from which the reverse transcriptase of the transformed yeast cell is derived.

A third object of the invention relates to a method for predicting the sensitivity of a reverse transcriptase to a NRTI compound, said method comprising the steps of:

i. producing a transformed yeast cell as previously described, comprising a reverse transcriptase indicator and a reverse transcriptase to be studied,
ii. contacting said transformed yeast cell with said NRTI compound,
iii. culturing the transformed yeast cell in a selective medium,
iv. determining the growth of the transformed yeast cell with or without NRTI compound, and
v. deducing therefrom if the reverse transcriptase to be studied is sensitive or resistant to said NRTI compound.

In one embodiment, an inhibition of growth after contacting the transformed yeast cells with the NRTI compound indicates that the reserve transcriptase to be studied is sensitive to said NRTI compound.

According to the invention, the term "inhibition of growth" includes any decrease in growth in said transformed yeast cell comprising a reverse transcriptase to be studied (tested transformed yeast cell) compared to a transformed yeast cell of the invention containing a reference reverse transcriptase known to be sensitive (reference transformed yeast cell).

Such an inhibition may be determined by measuring the ratio of the $IC_{50}$ values of the contacted NRTI compound for the tested transformed yeast cell versus for a reference transformed yeast cell ($IC_{50\ (studied\ RT)}/IC_{50\ (reference\ RT)}$).

According to the invention, a ratio $IC_{50\ (studied\ RT)}/IC_{50\ (reference\ RT)}$ lower than or equal to 1 indicates that the reverse transcriptase to be studied is sensitive to said NRTI compound; a ratio $IC_{50\ (studied\ RT)}/IC_{50\ (reference\ RT)}$ higher than 1 indicates that the reverse transcriptase to be studied is less sensitive to said NRTI compound than the reference reverse transcriptase.

Thus, in a preferred embodiment, said method comprises a further step after step (iv) consisting in determining the ratio of the $IC_{50}$ values of the contacted NRTI compound for the tested transformed yeast cell versus the $IC_{50}$ values of the contacted NRTI compound for a reference transformed yeast cell containing a reference reverse transcriptase known to be sensitive to said NRTI compound.

According to said preferred embodiment, a ratio lower than or equal to 1 indicates that the reserve transcriptase to be studied is sensitive to said NRTI compound.

According to the invention, the reverse transcriptase to be studied may be derived from a retrotransposon or a virus, particularly a retrovirus.

Particularly, said reverse transcriptase is derived from a retrovirus.

For example, the reverse transcriptase to be studied in this method may be derived from a retrovirus selected in the group comprising HIV-1 and HIV-2, simian immunodeficiency virus, avian immunodeficiency virus, bovine immunodeficiency virus, feline immunodeficiency virus or equine infectious anemic virus.

Thus, in a particular embodiment, the invention relates to a method for predicting the sensitivity of a reverse transcriptase derived from a retrovirus infecting a subject to a NRTI compound, said method comprising the steps of:

i. producing a transformed yeast cell as previously described, wherein the reverse transcriptase is derived from a retrovirus infecting said subject,
ii. contacting said transformed yeast cell with said NRTI compound,
iii. culturing the transformed yeast cell in a selective medium,
iv. determining the growth of the transformed yeast cell with or without NRTI compound, and
v. deducing therefrom if the reverse transcriptase derived from the retrovirus infecting said subject is sensitive or resistant to said NRTI treatment.

Preferably, said reverse transcriptase is a HIV-1 or HIV-2 reverse transcriptase (and said subject is a human patient infected by HIV-1 or HIV-2).

In one embodiment, an inhibition of growth after contacting the transformed yeast cells with the NRTI compound indicates that the reserve transcriptase of the retrovirus infecting the subject, and the retrovirus itself, is sensitive to said NRTI compound. Thus, the subject is likely to respond to said NRTI compound.

According to the invention, the term "inhibition of growth" includes any decrease in growth in the transformed yeast cell comprising the reverse transcriptase derived from a retrovirus infecting said subject (tested transformed yeast cell) compared to a transformed yeast cell of the invention containing a reference reverse transcriptase of said retrovirus known to be sensitive (reference transformed yeast cell).

Such an inhibition may be determined by determining the ratio of the $IC_{50}$ values of the contacted NRTI compound for the tested transformed yeast cell versus the $IC_{50}$ values of the contacted NRTI compound for a reference transformed yeast cell ($IC_{50\ (subject\ RT)}/IC_{50\ (reference\ RT)}$).

According to the invention, a ratio $IC_{50\ (subject\ RT)}/IC_{50\ (reference\ RT)}$ lower than or equal to 1 indicates that the reverse transcriptase to be studied is sensitive to said NRTI compound; the subject is likely to respond to a treatment based on said NRTI compound. A ratio $IC_{50\ (studied\ RT)}/IC_{50\ (reference\ RT)}$ higher than 1 indicates that the reverse transcriptase to be studied is less sensitive to said NRTI compound than the reference reverse transcriptase; the subject is at risk to not respond to a treatment based on said NRTI compound.

According to the invention, HIV-1 and HIV-2 reference reverse transcriptase may be respectively defined by nucleic acid sequences SEQ ID NO:1 and SEQ ID NO:2.

Preferably, the nucleic acid sequence coding for reverse transcriptase is under the control of an inducible promoter and reverse transcription (e.g. inducing the expression of the nucleic acid sequence encoding reverse transcriptase) is induced after contacting the tested NRTI compound with the transformed yeast cell of the invention.

According to the invention, a transformed yeast cell of the invention which has been contacted with a tested NRTI compound grows in a classical cell culture medium (which is not selective).

In still another embodiment of the invention, the reverse transcription indicator used in the transformed yeast cell is his3AI, and the selective medium used on step (ii) is a cell medium lacking in histidine.

In a preferred embodiment, said NRTI compound may be selected in the group comprising or consisting of Zidovudine, Didanosine, Stavudine, Lamivudine, Abacavir, Emtricitabine, Tenofovir and Zalcitabine.

In a particular embodiment, combinations of NRTI compounds may be tested. For example, combination of Tenofovir, Lamivudine, Abacavir and Emtricitabine, combination of Stavudine, Zidovudine and Didanosine could be tested.

In one embodiment, the invention relates to said method for predicting the resistance or sensitivity of a reverse transcriptase of a reverse transcriptase to a NRTI compound, wherein the NRTI to be tested is Zidovudine or Stavudine and wherein the transformed yeast cell comprises at least a nucleic acid coding for the nucleoside transporter CNT3.

In another particular embodiment, the invention relates to said method for predicting the resistance or sensitivity of a reverse transcriptase of a reverse transcriptase to a NRTI compound, wherein the NRTI to be tested is Zidovudine, Stavudine, Didanosine or Zalcitabine and wherein the transformed yeast cell comprises at least a nucleic acid sequence coding for the nucleoside transporter OAT1.

EXAMPLES

The following examples describe some of the preferred modes of making and practicing the present invention. However, it should be understood that the examples are for illustrative purposes only and are not meant to limit the scope of the invention.

Example 1

Activity of Thymidine Analog Reverse-Transcriptase Inhibitors on RT in Strain Carrying dCK and CNT3

*S. cerevisiae* strain A (Mat a, URA−, HIS−, LEU−) was transformed, using the standard Lithium Acetate protocol, with a PCR amplified DNA fragment having the nucleic acid sequence coding for the ura3 yeast gene. The transformed cell, Strain A1 (Mat a, URA+, HIS−, LEU−) has integrated the ura3 gene in its genomic locus. Strain A1 (Mat a, URA+, HIS−, LEU−) was transformed, using the standard Lithium Acetate protocol, with a previously linearized by StuI restriction enzyme p426GPDhdCK plasmid that contains the nucleic acid sequence coding for human dCK and ura3, and where linearization occurred within the ura3 open reading frame. The new strain (Strain A#), where integration of dCK occurred at the ura3 locus has the following phenotype (Mat a, URA−, HIS−, LEU−, dCK+).

Strain A# was transformed with an expression vector plasmid containing the nucleic acid sequence coding for the nucleoside transporter CNT3, and the plasmid pHART21 described in U.S. Pat. No. 5,714,313. HIV-1 RT activity in the resulted yeast strain and in non-modified Strain A was determined as described in U.S. Pat. No. 5,714,313 after 72 hours incubation in the presence or the absence of 200 μM of either AZT (Zidovudine) or d4T (Stavudine). NRTI dependent inhibition of HIV-1 RT took place when the foreign proteins were present (Table 1).

TABLE 1

Expression of dCK and CNT3 allows inhibiting HIV Reverse Transcriptase activity in yeast cells.

| | % Inhibition by AZT | % Inhibition by d4T |
|---|---|---|
| Strain A | 0% | 0% |
| Strain A# (dCK+, CNT3+) | 31% | 56% |

Example 2

RT Activity and Inhibitor Susceptibility in Strain Carrying dCK in its Genome and OAT1 in a Plasmid Strain A# (Mat a, URA−, HIS−, LEU−, dCK+) was transformed with an expression vector plasmid containing the nucleic acid sequence coding for the nucleoside transporter OAT1, and the plasmid pHART21 described in U.S. Pat. No. 5,714,313. HIV-1 RT activity in the resulted yeast strain and in non-modified Strain A (Mat a, URA−, HIS−, LEU−) was determined as described in U.S. Pat. No. 5,714,313 after 72 hours incubation in the presence or the absence of 100 μM of either AZT, ddC (Zalcitabine), ddI (Didanosine) or d4T. NRTI dependent inhibition of HIV-1 RT took place when the foreign proteins were present (FIG. 1).

Example 3

RT Activity and Inhibitor Susceptibility in Strain Carrying dCK and OAT1 in its Genome

*S. cerevisiae* strain B (Mat a, URA+, HIS−, LEU+) was transformed, using the standard Lithium Acetate protocol, with a previously linearized by StuI restriction enzyme p426GPDhdCK plasmid that contains the nucleic acid sequences coding for dCK and ura3, and where linearization occurred within the ura3 open reading frame. The new strain (Strain B#) where integration of dCK occurred at the ura3 locus has the following phenotype (Mat a, URA−, HIS−, LEU+, dCK+).

Figure 2:
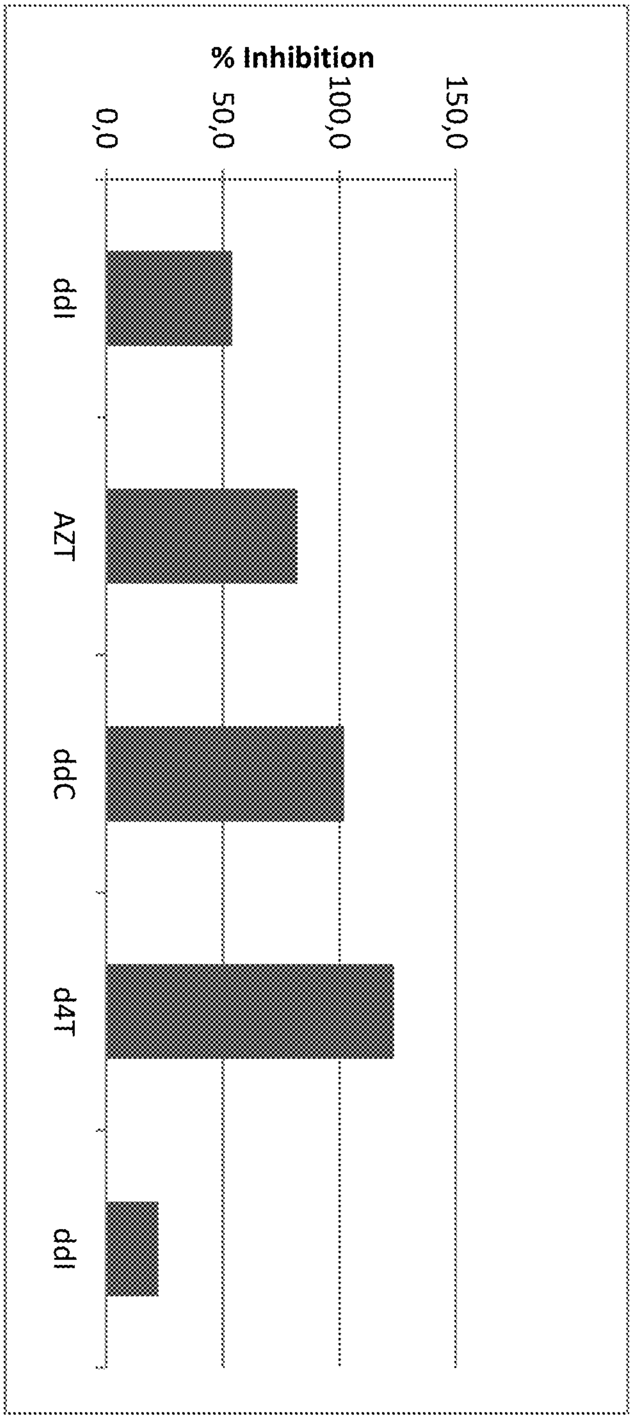
FIG. 2: RT activity and NRTI susceptibility in strain carrying dCK and OAT1 in its genome. The FIG. 2 shows that when the reverse transcriptase from HIV-1 is expressed, as described in U.S. Pat. No. 5,714,313, in genetically modified Strain B (Mat a, URA+, HIS−, LEU+) where both nucleic acid sequences coding for the dCK enzyme and OAT1 were integrated into the yeast genome (Strain B##: Mat a, URA−, HIS−, LEU−, dCK+, OAT1+), incubation for 72 hours in the presence of either ddC (ddc 100 μM), ddI (ddI 100 μM), AZT (AZT 100 μM) or d4T (d4T 100 μM), inhibits cell growth (% inhibition), and then reverse transcription, measured by absorbance at 600 nm.

Strain B# was genetically modified by standard methods through transformation with a PCR amplified DNA fragment. This nucleic acid fragment contains the nucleic acid sequence coding for OAT1 transporter flanked by 5' and 3' non-coding regions of the leu2 locus. The new modified strain where dCK and OAT1 are integrated in the yeast genome, Strain B## (Mat a, URA−, HIS−, LEU−, dCK+, OAT1+), was transformed with the plasmid pHART21 described in U.S. Pat. No. 5,714,313. HIV-1 RT activity in Strain B## was determined as described in U.S. Pat. No. 5,714,313 after 72 hours incubation in the presence of 100 μM of either AZT, ddC, ddI or d4T. NRTI dependent inhibition of HIV-1 RT took place when the foreign proteins were present (FIG. 2), showing that activity of those proteins is not related to the way they are expressed (as plasmid, FIG. 1, or in the yeast genome, FIG. 2).

Example 4

Determining $IC_{50}$ of NRTIs in Yeast Strain Carrying dCK and OAT1 in its Genome (Strain B##)

Figure 3:
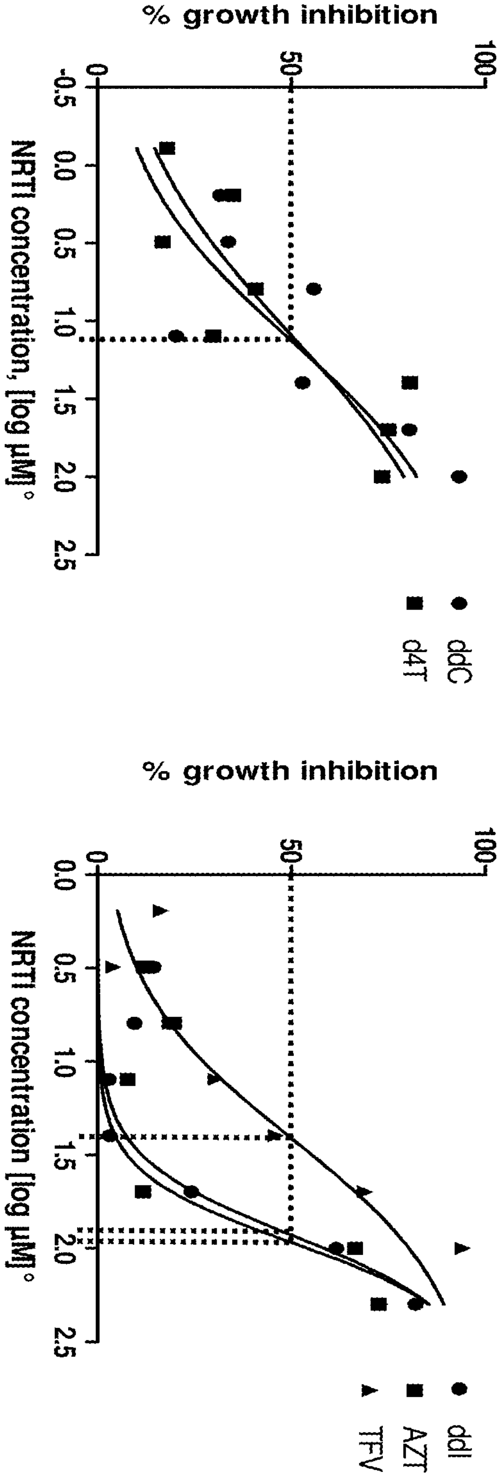
FIG. 3: $IC_{50}$ determination of NRTIs in yeast strain carrying dCK and OAT1 in its genome. Reverse transcriptase activity from HIV-1 was expressed and tested, in Strain B## (Mat a, URA−, HIS−, LEU−, dCK+, OAT1+) as described in U.S. Pat. No. 5,714,313, and incubated for 72 hours in the presence of different concentrations of either ddC, ddI, AZT, d4T or TFV Inhibition of cell growth, then reverse transcription, was measured by absorbance at 600 nm (OD @ 600 nm), and IC50 values were defined, for each inhibitor, as the inhibitor concentration inducing growth inhibition to 50%.

Determination of IC50 values of NRTIs to HIV-1 RT have been performed in Strain B## according to the method described in U.S. Pat. No. 5,714,313. After 72 hours incubation in the presence or the absence of different concentrations of either ddI, AZT, TFV (Tenofovir), ddC or d4T, cell growth was measured at OD at 600 nm. $IC_{50}$ values, defined as the amount (concentration) of NRTI inhibiting yeast growth to half (50%), were determined from plotting the percentage of growth inhibition versus NRTI concentration, expressed in logarithm scale (FIG. 3).

Example 5

Non-Efficiency of a Strain Carrying NT5C and Nucleoside Transporters Compared to Strain Carrying dCK and Nucleoside Transporters The cytosolic 5'-nucleotidase, NT5C, has been shown to have a phosphotransfer capacity (Johnson M A, Fridland 1989 A. Mol Pharmacol. 36:291-5 Phosphorylation of 2',3'-dideoxyinosine by cytosolic 5'-nucleotidase of human lymphoid cells) involved in NRTI phosphorylation. This protein was thus tested in a transformed yeast cell of the invention as a "dCK-like protein" and a construction similar to the invention comprising RT, RT indicator, NT5C and a nucleoside transporter was performed.

The nucleic acid sequence coding for the human cytosolic 5'-nucleotidase, NT5C was integrated in the yeast genome as follows. *S. cerevisiae* strain A1 (Mat a, URA+, HIS−, LEU−) was transformed, using the standard Lithium Acetate method, with a PCR amplified DNA fragment comprising a nucleic acid sequence identical to a 50 nucleotides length sequence upstream the start codon of the yeast ura3 gene, followed by the GPD promoter sequence, followed by the nucleic acid sequence coding for the 5' nucleotidase, followed by a nucleic acid sequence identical to a 50 nucleotides length sequence downstream the stop codon of the yeast ura3 gene. The modified yeast strain, Strain A§(Mat a, HIS−, LEU−, URA−, NT5C+) where the integration of the foreign gene occurred at the ura3 locus, was further transformed, following standard methods, with a plasmid harboring the nucleic acid coding sequence of the human nucleotide transporter CNT2 under the control of the ADH promoter. This strain was named Strain A§§(Mat a, HIS−, LEU+, URA−, NT5C+, CNT2+).

*S. cerevisiae* strain A# (Mat a, URA−, HIS−, LEU−, dCK+) from example 1, was transformed, using standard methods, with a plasmid harboring the nucleic acid coding sequence of the human nucleotide transporter CNT2 under the control of the ADH promoter. This strain was named Strain A#§(Mat a, URA−, HIS−, LEU+, dCK+, CNT2+).

HIV RT activity was determined in both strains as described in U.S. Pat. No. 5,714,313 as follows. Both HIV1 RT expressing strains were grown in SD-ura+glucose to saturation. 1 DO of saturated culture (about $10^7$ cells) was seeded in 1 ml SGal-ura and grew for 6 hrs. Glucose was then added to stop RT activation. After 12 hours, induced cells were seeded at 0.2 DO/ml in SD-His media and incubated for 72 hours. Incubations were performed at 30° C. with shaking Inhibition of HIV-1 RT activity was determined by measuring the inhibition of growth in the presence 200 μM concentration of ABC (Abacavir) or TFV (Tenofovir) inhibitors, as shown in Table II. The obtained results proved that the presence of dCK but not the presence of NT5C in yeast led to a substantial activity of NRTI inhibitors.

TABLE 2

HIV-1 Reverse transcriptase inhibition by Abacavir (ABC) and Tenofovir (TFV) determined in modified yeast cells.

| | % Inhibition by ABC | % Inhibition by TFV |
|---|---|---|
| Strain A§§ (NT5C+, CNT2+) | 0% | 0% |
| Strain A#§ (dCK+, CNT2+) | 87% | 96% |

The invention claimed is:

1. A method for determining the sensitivity of a reverse transcriptase to a nucleoside reverse transcriptase inhibitor (NRTI) compound selected from the group consisting of Zidovudine, Didanosine, Stavudine, Tenofovir, Zalcitabine and combinations thereof, said method comprising the steps of:

i. providing recombinant yeast cells comprising:
    a nucleic acid sequence coding for a reverse transcriptase,
    a reverse transcription indicator enabling selection of transformed yeast cells in which reverse transcription occurs,
    a nucleic acid sequence coding for deoxycytidine kinase (dCK), and
    a nucleic acid sequence coding for the nucleoside transporter OAT1,
ii. contacting said yeast cells separately with and without said NRTI compound,
iii. culturing the yeast cells in a selective medium,
iv. determining the growth of the yeast cells contacted with or without said NRTI compound, and
v. determining therefrom if the reverse transcriptase to be studied is sensitive or resistant to said NRTI compound, wherein a decrease in the growth of the yeast cells contacted with said NRTI compound of at least 30% relative to the growth of the yeast cells that are not contacted with said NRTI compound is indicative of reverse transcriptase sensitivity to said NRTI compound.

2. The method according to claim 1, wherein the reverse transcription indicator is his3AI and wherein the selective medium is a cell culture medium lacking histidine.

3. The method according to claim 1, wherein the reverse transcriptase is produced by HIV-1 or HIV-2 retrovirus.

4. The method according to claim 3, wherein the reverse transcriptase is produced by HIV-1 or HIV-2 retrovirus infecting a human patient.

5. The method according to claim 1, wherein the nucleic acid sequence coding for the reverse transcriptase is under the control of an inducible promoter, and the reverse transcriptase is induced after contacting the yeast cells with said NRTI compound.

6. The method according to claim 1, wherein a decrease in the growth of the yeast cells contacted with said NRTI compound of at least 90% relative to the growth of the yeast cells that are not contacted with said NRTI compound is indicative of reverse transcriptase sensitivity to said NRTI compound.

* * * * *

SEQUENCE LISTING

```
<160> NUMBER OF SEQ ID NOS: 16

<210> SEQ ID NO 1
<211> LENGTH: 1683
<212> TYPE: DNA
<213> ORGANISM: Human Immunodeficiency Virus type 1

<400> SEQUENCE: 1

cccattagcc ctattgagac tgtaccagta aaattaaagc ccgggatgga tggcccaaaa      60

gttaaacaat ggccattgac agaagaaaaa ataaaagcat tagtagaaat ttgtacagag     120

atggaaaagg aagggaaaat ttcaaaaatt gggcctgaaa atccatacaa tactccagta     180

tttgccataa agaaaaaaga cagtactaaa tggagaaaat tagtagattt cagagaactt     240

aataagagaa ctcaagactt ctgggaagtt caattaggaa taccacatcc cgcagggtta     300

aaaaagaaaa aatcagtaac agtactggat gtgggtgatg catatttttc agttccctta     360

gatgaagact tcaggaagta tactgcattt accataccta gtataaacaa tgagacacca     420

gggattagat atcagtacaa tgtgcttcca cagggatgga aaggatcacc agcaatattc     480

caaagtagca tgacaaaaat cttagagcct tttagaaaac aaaatccaga catagttatc     540

tatcaataca tggatgattt gtatgtagga tctgacttag aaatagggca gcatagaaca     600

aaaatagagg agctgagaca acatctgttg aggtggggac ttaccacacc agacaaaaaa     660

catcagaaag aacctccatt cctttggatg ggttatgaac tccatcctga taaatggaca     720
```

-continued gtacagccta tagtgctgcc agaaaaagac agctggactg tcaatgacat acagaagtta 780
gtggggaaat tgaattgggc aagtcagatt tacccaggga ttaaagtaag gcaattatgt 840
aaactcctta gaggaaccaa agcactaaca gaagtaatac cactaacaga agaagcagag 900
ctagaactgg cagaaaacag agagattcta aaagaaccag tacatggagt gtattatgac 960
ccatcaaaag acttaatagc agaaatacag aagcaggggc aaggccaatg gacatatcaa 1020
atttatcaag agccatttaa aaatctgaaa acaggaaaat atgcaagaat gaggggtgcc 1080
cacactaatg atgtaaaaca attaacagag gcagtgcaaa aaataaccac agaaagcata 1140
gtaatatggg gaaagactcc taaatttaaa ctgcccatac aaaaggaaac atgggaaaca 1200
tggtggacag agtattggca agccacctgg attcctgagt gggagtttgt taatacccct 1260
cccttagtga aattatggta ccagttagag aaagaaccca tagtaggagc agaaaccttc 1320
tatgtagatg gggcagctaa cagggagact aaattaggaa aagcaggata tgttactaat 1380
agaggaagac aaaaagttgt caccctaact gacacaacaa atcagaagac tgagttacaa 1440
gcaatttatc tagctttgca ggattcggga ttagaagtaa acatagtaac agactcacaa 1500
tatgcattag gaatcattca agcacaacca gatcaaagtg aatcagagtt agtcaatcaa 1560
ataatagagc agttaataaa aaaggaaaag gtctatctgg catgggtacc agcacacaaa 1620
ggaattggag gaaatgaaca agtagataaa ttagtcagtg ctggaatcag gaaagtacta 1680
tag 1683

<210> SEQ ID NO 2
<211> LENGTH: 1686
<212> TYPE: DNA
<213> ORGANISM: Human Immunodeficiency Virus type 2

<400> SEQUENCE: 2
atggcagtcg ccaaagtaga gccaataaaa ataatgctaa agccaggaaa agatggacca 60
aaactgagac aatggccctt aacaaaagaa aaaatagaag cattaaaaga aatctgtgaa 120
aaaatggaaa aagaaggcca gctagaggaa gcacctccaa ctaatcctta taatacccc 180 acatttgcaa tcaagaaaaa ggacaaaaac aaatggagga tgctaataga tttcagagaa 240
ctaaacaagg taactcaaga tttcacagaa attcagttag gaattccaca cccagcagga 300
ttggccaaga agagaagaat tactgtacta gatgtagggg atgcttactt ttccatacca 360
ctacatgagg actttagacc atatactgca tttactctac catcagtgaa caatgcagaa 420
ccaggaaaaa gatacatata taaagtcttg ccacagggat ggaagggatc accagcaatt 480
tttcaacaca caatgagaca ggtattagaa ccattcagaa aagcaaacaa ggatgtcatc 540
atcattcagt acatggatga tatcttaata gctagtgaca ggacagattt agaacatgac 600
agggtaatcc tgcaactcaa ggaacttcta aatggcctag gattttctac cccagatgag 660
aagttccaaa aagacccgcc ataccactgg atgggttatg aactatggcc aactaaatgg 720
aagttgcaga aaatacagtt gccccaaaaa gaaatatgga cagtcaatga catccagaag 780
ctagtgggtg tcctaaattg ggcagcacaa ctctacccag ggataaagac caaacactta 840
tgtaggttaa tcagaggaaa aatgacactc acagaagaag tacagtggac agaattagca 900
gaagcagagc tagaagaaaa cagaattatc ctaagccagg aacaagaggg acactattac 960
caagaagaaa aagagttaga agcaacagtc caaaaggatc aagacaatca gtggacatat 1020
aaaatacacc aggaagacaa aattctaaaa gtaggaaagt atgcaaaggt aaaaaacacc 1080

-continued cataccaatg gaatcagatt gttagcacag gtagttcaaa aaataggaaa agaagcactg 1140
gtcatttggg gacgaatacc gaaatttcac ctaccagtag agagggaaat ctgggagcaa 1200
tggtgggata actactggca agtgacatgg atcccagact gggacttcgt gtctacccca 1260
ccactggtca ggttagcgtt taacctggta ggggatccta taccaggtgc agagaccttc 1320
tacacagatg gatcctgcaa taggcaatca aaagaaggaa aagcaggata tgtaacagat 1380
agagggaaag acaaggtaaa gaaactagag caaactacca atcagcaagc agaattagaa 1440
gcctttgcga tggcactaac agactcgggt ccaaaagtta atattatagt agactcacag 1500
tatgtaatgg gaatagtagc aagccaacca acagagtcag aaagtaaaat agtgaaccag 1560
atcatagaag aaatgataaa aaaggaagca atctatgttg catgggtccc agcccacaaa 1620
ggcatagggg gaaaccagga agtagatcat ttagtgagtc agggtatcag acaagtgttg 1680
taatag 1686

<210> SEQ ID NO 3
<211> LENGTH: 17
<212> TYPE: DNA
<213> ORGANISM: Artificial
<220> FEATURE:
<223> OTHER INFORMATION: primers
<220> FEATURE:
<221> NAME/KEY: N
<222> LOCATION: (8)..(8)
<223> OTHER INFORMATION: N = A, T, G or C
<220> FEATURE:
<221> NAME/KEY: misc_feature
<222> LOCATION: (8)..(8)
<223> OTHER INFORMATION: n is a, c, g, or t
<220> FEATURE:
<221> NAME/KEY: N
<222> LOCATION: (15)..(15)
<223> OTHER INFORMATION: N = A or G
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: N
<222> LOCATION: (16)..(16)
<223> OTHER INFORMATION: N = A or G

<400> SEQUENCE: 3
ccagtaanat taaancc 17

<210> SEQ ID NO 4
<211> LENGTH: 17
<212> TYPE: DNA
<213> ORGANISM: Artificial
<220> FEATURE:
<223> OTHER INFORMATION: primers

<400> SEQUENCE: 4
attcaagcac aaccaga 17

<210> SEQ ID NO 5
<211> LENGTH: 17
<212> TYPE: DNA
<213> ORGANISM: Artificial
<220> FEATURE:
<223> OTHER INFORMATION: primers

<400> SEQUENCE: 5
ccaataaaaa taatgct 17

-continued

<210> SEQ ID NO 6
<211> LENGTH: 17
<212> TYPE: DNA
<213> ORGANISM: Artificial
<220> FEATURE:
<223> OTHER INFORMATION: primers

<400> SEQUENCE: 6
agtcaatgac atccaga 17

<210> SEQ ID NO 7
<211> LENGTH: 783
<212> TYPE: DNA
<213> ORGANISM: Homo sapiens

<400> SEQUENCE: 7
atggccaccc cgcccaagag aagctgcccg tctttctcag ccagctctga ggggacccgc 60
atcaagaaaa tctccatcga agggaacatc gctgcaggga agtcaacatt tgtgaatatc 120
cttaaacaat tgtgtgaaga ttgggaagtg gttcctgaac ctgttgccag atggtgcaat 180
gttcaaagta ctcaagatga atttgaggaa cttacaatgt ctcagaaaaa tggtgggaat 240
gttcttcaga tgatgtatga gaaacctgaa cgatggtctt ttaccttcca aacatatgcc 300
tgtctcagtc gaataagagc tcagcttgcc tctctgaatg gcaagctcaa agatgcagag 360
aaatctgtat tattttttga acgatctgtg tatagtgaca ggtatatttt tgcatctaat 420
ttgtatgaat ctgaatgcat gaatgagaca gagtggacaa tttatcaaga ctggcatgac 480
tggatgaata accaatttgg ccaaagcctt gaattggatg gaatcattta tcttcaagcc 540
actccagaga catgcttaca tagaatatat ttacggggaa gaaatgaaga gcaaggcatt 600
cctcttgaat atttagagaa gcttcattat aaacatgaaa gctggctcct gcataggaca 660
ctgaaaacca acttcgatta tcttcaagag gtgcctatct taacactgga tgttaatgaa 720
gactttaaag acaaatatga aagtctggtt gaaaaggtca aagagttttt gagtactttg 780
tag 783

<210> SEQ ID NO 8
<211> LENGTH: 2107
<212> TYPE: DNA
<213> ORGANISM: homo sapiens

<400> SEQUENCE: 8
ctgcagcgag agcgcgcgga tctcagcgcg ggagcagtgc ttctgcggca ggcccctgag 60
ggagggagct gtcagccagg gaaaaccgag aacaccatca ccatgacaac cagtcaccag 120
cctcaggaca gatacaaagc tgtctggctt atcttcttca tgctgggtct gggaacgctg 180
ctcccgtgga attttttcat gacggccact cagtatttca caaaccgcct ggacatgtcc 240
cagaatgtgt ccttggtcac tgctgaactg agcaaggacg cccaggcgtc agccgcccct 300
gcagcaccct tgcctgagcg gaactctctc agtgccatct tcaacaatgt catgacccta 360
tgtgccatgc tgcccctgct gttattcacc tacctcaact ccttcctgca tcagaggatc 420
ccccagtccg tacggatcct gggcagcctg gtggccatcc tgctggtgtt tctgatcact 480
gccatcctgg tgaaggtgca gctggatgct ctgcccttct ttgtcatcac catgatcaag 540
atcgtgctca ttaattcatt tggtgccatc ctgcagggca gcctgtttgg tctggctggc 600
cttctgcctg ccagctacac ggccccccatc atgagtggcc agggcctagc aggcttcttt 660
gcctccgtgg ccatgatctg cgctattgcc agtggctcgg agctatcaga aagtgccttc 720

-continued ggctacttta tcacagcctg tgctgttatc attttgacca tcatctgtta cctgggcctg 780
ccccgcctgg aattctaccg ctactaccag cagctcaagc ttgaaggacc cggggagcag 840
gagaccaagt tggacctcat tagcaaagga gaggagccaa gagcaggcaa agaggaatct 900
ggagtttcag tctccaactc tcagcccacc aatgaaagcc actctatcaa agccatcctg 960
aaaaatatct cagtcctggc tttctctgtc tgcttcatct tcactatcac cattgggatg 1020
tttccagccg tgactgttga ggtcaagtcc agcatcgcag gcagcagcac ctgggaacgt 1080
tacttcattc ctgtgtcctg tttcttgact ttcaatatct ttgactggtt gggccggagc 1140
ctcacagctg tattcatgtg gcctgggaag gacagccgct ggctgccaag cctggtgctg 1200
gcccggctgg tgtttgtgcc actgctgctg ctgtgcaaca ttaagccccg ccgctacctg 1260
actgtggtct tcgagcacga tgcctggttc atcttcttca tggctgcctt tgccttctcc 1320
aacggctacc tcgccagcct ctgcatgtgc ttcgggccca agaaagtgaa gccagctgag 1380
gcagagaccg caggagccat catggccttc ttcctgtgtc tgggtctggc actgggggct 1440
gttttctcct tcctgttccg ggcaattgtg tgacaaagga tggacagaag gactgcctgc 1500
ctccctccct gtctgcctcc tgccccttcc ttctgccagg ggtgatcctg agtggtctgg 1560
cggttttttc ttctaactga cttctgcttt ccacggcgtg tgctgggccc ggatctccag 1620
gccctgggga gggagcctct ggacggacag tggggacatt gtgggtttgg ggctcagagt 1680
cgagggacgg ggtgtagcct cggcatttgc ttgagtttct ccactcttgg ctctgactga 1740
tccctgcttg tgcaggccag tggaggctct tgggcttgga gaacacgtgt gtctctgtgt 1800
atgtgtctgt gtgtctgcgt ccgtgtctgt cagactgtct gcctgtcctg gggtggctag 1860
gagctgggtc tgaccgttgt atggtttgac ctgatatact ccattctccc ctgcgcctcc 1920
tcctctgtgt tctctccatg tccccctccc aactccccat gcccagttct tacccatcat 1980
gcaccctgta cagttgccac gttactgcct tttttaaaaa tatatttgac agaaaccagg 2040
tgccttcaga ggctctctga tttaaataaa cctttcttgt ttttttaaaa aaaaaaaaaa 2100
aaaaaaa 2107

<210> SEQ ID NO 9
<211> LENGTH: 2276
<212> TYPE: DNA
<213> ORGANISM: homo sapiens

<400> SEQUENCE: 9
ggagcggctc tggcatcacc tcggagctga cgaagcggga agagccccgc accagtgctg 60
cccctacaga gctctcggcg gggggtggag gcgcatccgc cgcggcggcc atggcgcgag 120
gagacgcccc gcgggacagc taccacctgg tcgggatcag cttcttcatc ctggggctgg 180
gcaccctcct tccctggaac ttcttcatca ccgccatccc gtacttccag gcgcgactgg 240
ccggggccgg caacagcaca gccaggatcc tgagcaccaa ccacacgggt cccgaggatg 300
ccttcaactt caaccattgg gtgacgctgc tgtcccagct gcccctgctg ctcttcaccc 360
tcctcaactc cttcctgtac cagtgcgtcc cggagacggt gcgcattctg ggcagcctgc 420
tggccatact gctgctcttt gccctgacag cagcgctggt caaggtggac atgagccccg 480
gacccttctt ctccatcacc atggcctccg tctgcttcat caactccttc agtgcagtcc 540
tacagggcag cctcttcggg cagctgggca ccatgccctc cacctacagc accctcttcc 600
tcagcggcca gggcctggct gggatctttg ctgcccttgc catgctcctg gccatggcca 660
gtggcgtgga cgccgagacc tctgccctgg ggtactttat cacgccctgt gtgggcatcc 720
tcatgtccat cgtgtgttac ctgagcctgc ctcacctgaa gtttgcccgc tactacctgg 780
ccaataaatc atcccaggcc caagctcagg agctggagac caaagctgag ctcctccagt 840
ctgatctggc tgacagcgct gtgccttgtg ttggtcttca cagtcaccct gtccgtcttc 900
cccgccatca cagccatggt gaccagctcc accagtcctg ggaagtggag tcagttcttc 960
aaccccatct gctgcttcct cctcttcaac atcatggact ggctgggacg gagcctgacc 1020
tcttacttcc tgtggccaga cgaggacagc cggctgctgc ccctgctggt ctgcctgcgg 1080
ttcctgttcg tgcccctctt catgctgtgc cacgtgcccc agaggtcccg gctgcccatc 1140
ctcttcccac aggatgccta cttcatcacc ttcatgctgc tctttgccgt ttctaatggc 1200
tacctggtgt ccctcaccat gtgcctggcg cccaggcagg tgctgccaca cgagagggag 1260
gtggccggcg ccctcatgac cttcttcctg gccctgggac tttcctgtgg agcctccctc 1320
tccttcctct tcaaggcgct gctctgaagt ggcccctcca ggctctttgg cagcctcttc 1380
tcgacgtctc cttccggagc tgagatccag cccagggcga atggcgagct tggctcaggc 1440
ctctgcgggg tggaggcccc tgggcctgag gctgccagca gcgggcagga gctgctcttc 1500
atccacttgg agtgctgcgg ggaagaaatc accaccggtc attctaaccc tcacccagga 1560
atgggggtga ctcgcacaag acctcatgga aagggtgatg actagggaaa agagggtgca 1620
gggcacggct gctccccacc accaggtctg catttgttca tcatcatcag gagcagaggt 1680
gaccagaggg ttcagagtgg gaggcagggc cagcccaggc caggagcgcc tcatcttccc 1740
aggcctcagc cacccagggt aaaaggtgcc agggaagttg tgggcacctg agaggaggaa 1800
cagatgtgga ggacctgagg gtgctcaaag ggccaggctc agcctcaagc agtgttttca 1860
ttgccaacac ttactgtacc cactccgcag agccccgctg ggcctgggcc ccagggccac 1920
agctagcctg catgtgtgta ctgcacttta cagtttgcaa agctcttcca tacccactct 1980
ctcaccgaag cctaattgag gctcttggaa ggagtcaggc aaggattgtg cttcccccat 2040
tatacaggtg acaaaactga gtcctgggga aagtgactgg tccgtggtag agccgggacc 2100
caatcccctc tctctcctcc ctgttggtgc tgttcttcct gcccaacacc tgtttctctt 2160
ttcctcaagg ggtttggggc aggagcctgg gcacttactc cccgtttttg ctgtttctcc 2220
ttctgaccct gctcttgggt ctaataaccc catttatttg taaaaaaaaa aaaaaa 2276

<210> SEQ ID NO 10
<211> LENGTH: 2421
<212> TYPE: DNA
<213> ORGANISM: homo sapiens

<400> SEQUENCE: 10
aaggcaagcc agagccaaag caggttggac ccagcttgtc cccacagaga cgtgtgcttc 60
cctctctctc tgagagcgac ctgttaaccg caaatacctg gaaggtctgg gacatggaga 120
acgacccctc gagacgaaga gagtccatct ctctcacacc tgtggccaag ggtctggaga 180
acatgggggc tgatttcttg gaaagcctgg aggaaggcca gctccctagg agtgacttga 240
gccccgcaga gatcaggagc agctggagcg aggcggcgcc gaagcccttc tccagatgga 300
ggaacctgca gccagccctg agagccagaa gcttctgcag ggagcacatg cagctgtttc 360
gatggatcgg cacaggcctg ctctgcactg ggctctctgc cttcctgctg gtggcctgcc 420
tcctggattt ccagagggcc ctggctctgt ttgtcctcac ctgtgtggtc ctcaccttcc 480
tgggccaccg cctgctgaaa cggcttctgg ggccaaagct gaggaggttt ctcaagcctc 540

-continued

```
agggccatcc ccgcctgctg ctctggttta agaggggtct agctcttgct gctttcctgg    600

gcctggtcct gtggctgtct ctggacacct cccagcggcc tgagcaactg gtgtccttcg    660

caggaatctg cgtgttcgtc gctctcctct ttgcctgctc aaagcatcat tgcgcagtgt    720

cctggagggc cgtgtcttgg ggacttggac tgcagtttgt acttggactc ctcgtcatca    780

gaacagaacc aggattcatt gcgttcgagt ggctgggcga gcagatccgg atcttcctga    840

gctacacgaa ggctggctcc agcttcgtgt ttggggaggc gctggtcaag gatgtctttg    900

cctttcaggt tctgcccatc attgtctttt tcagctgtgt catatccgtt ctctaccacg    960

tgggcctcat gcagtgggtg atcctgaaga ttgcctggct gatgcaagtc accatgggca   1020

ccacagccac tgagaccctg agtgtggctg gaaacatctt tgtgagccag accgaggctc   1080

cattactgat ccggccctac ttggcagaca tgacactctc tgaagtccac gttgtcatga   1140

ccggaggtta cgccaccatt gctggcagcc tgctgggtgc ctacatctcc tttgggatcg   1200

atgccacctc gttgattgca gcctctgtga tggctgcccc ttgtgccttg gccctctcca   1260

aactggtcta cccggaggtg gaggagtcca agtttaggag ggaggaagga gtgaaactga   1320

cctatggaga tgctcagaac ctcatagaag cagccagcac tggggccgcc atctccgtga   1380

aggtggtcgc caacatcgct gccaacctga ttgcgttcct ggctgtgctg gactttatca   1440

atgctgccct ctcctggctg ggagacatgg tggacatcca ggggctcagc ttccagctca   1500

tctgctccta catcctgcgg cctgtagcct tcttgatggg tgtggcgtgg gaggactgcc   1560

cagtggtagc tgagctgctg gggatcaagc tgtttctgaa cgagtttgtg gcctatcaag   1620

acctctccaa gtacaagcaa tgccgcctgg caggggccga ggagtgggtc ggcgacagga   1680

agcagtggat ctccgtcaga gctgaagtcc tcacgacgtt tgccctctgt ggatttgcca   1740

atttcagctc cattgggatc atgctgggag gcttgacctc catggtcccc caacggaaga   1800

gcgacttctc ccagatagtg ctccgggcgc tcttcacggg agcctgtgtg tccctggtga   1860

acgcctgtat ggcagggatc ctctacatgc ccagggggc tgaagttgac tgcatgtccc    1920

tcttgaacac gaccctcagc agcagtagct ttgagattta ccagtgctgc cgtgaggcct   1980

tccagagcgt caatccagag ttcagcccag aggccctgga caactgctgt cggttttaca   2040

accacacgat ctgtgcacag tgaggacaga acatgcttgt gcttctgcgc ttctgagggc   2100

tgttctcccc cgggaaccat ctgtccccac cttccctttc ccagagccct cttcagggaa   2160

gccacaggac ttagacccag ctcaatccca caattgggaa ggggtcatgg agtgagtgtg   2220

cagagagtga gtgaggacat aaggaaggac atgtcccact ccatccccct tcctgctccc   2280

ccatttccta actcccccag tgtgaattct cagggtcact tctgcctcct cccgtttccc   2340

ctccacatcc aaacagcacc ctggtcctct ctatcccccc tctcctgggg tccctcacat   2400

gccccttccc ttctgttgtg g                                              2421
```

<210> SEQ ID NO 11
<211> LENGTH: 2095
<212> TYPE: DNA
<213> ORGANISM: homo sapiens

<400> SEQUENCE: 11

```
ccccaagctg ggttgaggag aacaggagat ggagaaagca agtggaagac agtccattgc     60

tctgtccaca gtggagactg gcacagtgaa cccggggctg gagctcatgg aaaaagaagt    120

agagcctgag ggaagcaaga ggactgacgc acaaggacac agcctggggg atggactggg    180

cccttccact taccagagga ggagtcggtg gcctttcagc aaagcaagaa gtttctgcaa    240
```

aacacacgcc agcttgttca agaagatcct gttgggcctg ttgtgtttgg cctatgctgc 300
ctatctccta gcagcttgca tcttgaattt ccagagggca ctggccttgt ttgtcatcac 360
ctgcttggtg atctttgtcc tggttcactc gtttttgaaa aagctcctgg gcaaaaaatt 420
aacaagatgt ctgaagccct ttgaaaactc ccgcctgagg ctttggacga aatgggtgtt 480
tgcaggagtc tccttggttg gccttatact gtggttggct ttagacacag cccaaaggcc 540
agagcagctg atcccctttg caggaatctg catgttcatc cttatcctct ttgcctgctc 600
caaacaccac agcgcagtgt cctggaggac agtgttttcg ggcctaggtc ttcaatttgt 660
ctttgggatc ttggtcatca gaactgatct tggatatact gtatttcagt ggctgggaga 720
gcaggtccag attttcctga actacactgt ggccggctcc agttttgtct ttggggatac 780
actggtcaag gatgtctttg cttttcaggc cttaccaatc atcattttct ttggatgtgt 840
ggtgtccatt ctctactacc tgggccttgt gcaatgggta gttcagaagg tcgcctggtt 900
tttacaaatc actatgggca ccactgctac agagaccctg gctgtggcag gaaacatctt 960
tgtgggtatg acagaggcac ctctgctcat ccgtccctac cttggggaca tgacactctc 1020
tgaaatccat gcggtgatga ctggagggtt tgccaccatt tctggcactg tgctgggagc 1080
cttcatagcc tttggggttg atgcatcatc cctgatttct gcctctgtga tggccgcccc 1140
ttgtgctctc gcctcatcaa agctagcgta tccggaagtg gaggagtcca agttcaagag 1200
tgaggagggg gtaaagctgc cccgtgggaa ggagaggaat gtcctggaag ctgccagcaa 1260
cggagccgta gatgccatag gccttgctac taatgtagca gccaacctga ttgccttttt 1320
ggctgtgttg gccttcatca atgctgccct ctcctggctg ggggaattgg tggacataca 1380
ggggctcact ttccaggtca tctgctccta tctcctaagg cccatggttt tcatgatggg 1440
tgtagagtgg acagactgtc caatggtggc tgagatggtg ggaatcaagt tcttcataaa 1500
tgagtttgtg gcttatcagc aactgtctca atacaagaac aaacgtctct ctggaatgga 1560
ggagtggatt gagggagaga aacagtggat ttctgtgaga gctgaaatca ttacaacatt 1620
ttcactctgt ggatttgcca atcttagttc cataggaatc acacttggag gcttgacatc 1680
aatagtacct caccggaaga gtgacttgtc caaggttgtg gtcagggccc tcttcacagg 1740
ggcctgtgta tcccttatca gtgcctgtat ggcaggaatc ctctatgtcc ccaggggagc 1800
tgaagctgac tgtgtctcct tcccaaacac aagtttcacc aatagaacct atgagaccta 1860
catgtgctgc agagggctct ttcagagtac ttctctgaat ggcaccaacc ctccttcttt 1920
ttctggtccc tgggaagata aggagttcag tgctatggcc cttactaact gctgtggatt 1980
ctacaacaat accgtctgtg cctaaggctg cttgatctat ttctataaca gttttgatct 2040
taaaagcttt gtgattgcaa aggtgtttat gtactcaggg tgcccacaac tcact 2095

<210> SEQ ID NO 12
<211> LENGTH: 2209
<212> TYPE: DNA
<213> ORGANISM: homo sapiens

<400> SEQUENCE: 12
ctaaatgaag agcgcttggg acctgaacaa ccagcagcga tacccaggta caaaggacct 60
ccagaccaga gccagccagc agcaaaaaga gcatggagct gaggagtaca gcagccccca 120
gagctgaggg ctacagcaac gtgggcttcc agaatgaaga aaactttctt gagaacgaga 180
acacatcagg aaacaactca ataagaagca gagctgtgca aagcagggag cacacaaaca 240

```
ccaaacagga tgaagaacag gtcacagttg agcaggattc tccaagaaac agagaacaca    300
tggaggatga tgatgaggag atgcaacaaa aagggtgttt ggaaaggagg tatgacacag    360
tatgtggttt ctgtaggaaa cacaaaacaa ctcttcggca catcatctgg ggcattttat    420
tagcaggtta tctggttatg gtgatttcgg cctgtgtgct gaactttcac agagcccttc    480
ctctttttgt gatcaccgtg gctgccatct tctttgttgt ctgggatcac ctgatggcca    540
aatacgaaca tcgaattgat gagatgctgt ctcctggcag aaggcttcta aacagccatt    600
ggttctggct gaagtgggtg atctggagct ccctggtcct agcagttatt ttctggttgg    660
cctttgacac tgccaaattg ggtcaacagc agctggtgtc cttcggtggg ctcataatgt    720
acattgtcct gttatttcta ttttccaagt acccaaccag agtttactgg agacctgtct    780
tatggggaat cgggctacag tttcttcttg ggctcttgat tctaaggact gaccctggat    840
ttatagcttt tgattggttg ggcagacaag ttcagacttt tctggagtac acagatgctg    900
gtgcttcatt tgtctttggt gagaaataca aagaccactt ctttgcattt aaggtcctgc    960
cgatcgtggt tttcttcagc actgtgatgt ccatgctgta ctacctggga ctgatgcagt   1020
ggattattag aaaggttgga tggatcatgc tagttactac gggatcatct cctattgaat   1080
ctgtagttgc ttctggcaat atatttgttg gacaaacgga gtctccactg ctggtccgac   1140
catatttacc ttacatcacc aagtctgaac tccacgccat catgaccgcc gggttctcta   1200
ccattgctgg aagcgtgcta ggtgcataca tttcttttgg ggttccatcc tcccacttgt   1260
taacagcgtc agttatgtca gcacctgcgt cattggctgc tgctaaactc ttttggcctg   1320
agacagaaaa acctaaaata accctcaaga atgccatgaa aatggaaagt ggtgattcag   1380
ggaatcttct agaagctgca acacagggag catcctcctc catctccctg gtggccaaca   1440
tcgctgtgaa tctgattgcc ttcctggccc tgctgtcttt tatgaattca gccctgtcct   1500
ggtttggaaa catgtttgac tacccacagc tgagttttga gctaatctgc tcctacatct   1560
tcatgccctt ttccttcatg atgggagtgg aatggcagga cagctttatg gttgccagac   1620
tcataggtta taagaccttc ttcaatgaat ttgtggctta tgagcacctc tcaaaatgga   1680
tccacttgag gaaagaaggt ggacccaaat ttgtaaacgg tgtgcagcaa tatatatcaa   1740
ttcgttctga gataatcgcc acttacgctc tctgtggttt tgccaatatc gggtccctag   1800
gaatcgtgat cggcggactc acatccatgg ctccttccag aaagcgtgat atcgcctcgg   1860
gggcagtgag agctctgatt gcggggaccg tggcctgctt catgacagcc tgcatcgcag   1920
gcatactctc cagcactcct gtggacatca actgccatca cgttttagag aatgccttca   1980
actccacttt ccctggaaac acaaccaagg tgatagcttg ttgccaaagt ctgttgagca   2040
gcactgttgc caagggtcct ggtgaagtca tcccaggagg aaaccacagt ctgtattctt   2100
tgaagggctg ctgcacattg ttgaatccat cgacctttaa ctgcaatggg atctctaata   2160
cattttgagg tcagccactt ctccagtgga actctgaagt acagatgct               2209
```

<210> SEQ ID NO 13
<211> LENGTH: 2180
<212> TYPE: DNA
<213> ORGANISM: homo sapiens

<400> SEQUENCE: 13

```
caagggtcag gtctccagca gaccctgaaa gctgagctgc cctgaccccc aaagtgagga     60
gaagctgcaa gggaaaaggg agggacagat cagggagacc ggggaagaag gaggagcagc    120
caaggaggct gctgtccccc cacagagcag ctcggactca gctcccggag caacccagct    180
```

-continued

```
gcggaggcaa cggcagtgct gctcctccag cgaaggacag caggcaggca gacagacaga    240

ggtcctggga ctggaaggcc tcagccccca gccactgggc tgggcctggc ccaatggcct    300

ttaatgacct cctgcagcag gtggggggtg tcggccgctt ccagcagatc caggtcaccc    360

tggtggtcct ccccctgctc ctgatggctt ctcacaacac cctgcagaac ttcactgctg    420

ccatccctac ccaccactgc cgcccgcctg ccgatgccaa cctcagcaag aacggggggc    480

tggaggtctg gctgccccgg gacaggcagg ggcagcctga gtcctgcctc cgcttcacct    540

ccccgcagtg gggactgccc tttctcaatg gcacagaagc caatggcaca ggggccacag    600

agccctgcac cgatggctgg atctatgaca acagcacctt cccatctacc atcgtgactg    660

agtgggacct tgtgtgctct cacagggccc tacgccagct ggcccagtcc ttgtacatgg    720

tgggggtgct gctcggagcc atggtgttcg gctaccttgc agacaggcta ggccgccgga    780

aggtactcat cttgaactac ctgcagacag ctgtgtcagg gacctgcgca gccttcgcac    840

ccaacttccc catctactgc gccttccggc tcctctcggg catggctctg gctggcatct    900

ccctcaactg catgacactg aatgtggagt ggatgcccat tcacacacgg gcctgcgtgg    960

gcaccttgat tggctatgtc tacagcctgg gccagttcct cctggctggt gtggcctacg   1020

ctgtgcccca ctggcgccac ctgcagctac tggtctctgc gcctttttt gccttcttca   1080

tctactcctg gttcttcatt gagtcggccc gctggcactc ctcctccggg aggctggacc   1140

tcaccctgag ggccctgcag agagtcgccc ggatcaatgg gaagcgggaa gaaggagcca   1200

aattgagtat ggaggtactc cgggccagtc tgcagaagga gctgaccatg ggcaaaggcc   1260

aggcatcggc catggagctg ctgcgctgcc ccaccctccg ccacctcttc ctctgcctct   1320

ccatgctgtg gtttgccact agctttgcat actatgggct ggtcatggac ctgcagggct   1380

ttggagtcag catctaccta atccaggtga tctttggtgc tgtggacctg cctgccaagc   1440

ttgtgggctt ccttgtcatc aactccctgg gtcgccggcc tgcccagatg gctgcactgc   1500

tgctggcagg catctgcatc ctgctcaatg gggtgatacc ccaggaccag tccattgtcc   1560

gaacctctct tgctgtgctg gggaagggtt gtctggctgc ctccttcaac tgcatcttcc   1620

tgtatactgg ggaactgtat cccacaatga tccggcagac aggcatggga atgggcagca   1680

ccatggcccg agtgggcagc atcgtgagcc cactggtgag catgactgcc gagctctacc   1740

cctccatgcc tctcttcatc tacggtgctg ttcctgtggc cgccagcgct gtcactgtcc   1800

tcctgccaga gaccctgggc cagccactgc cagacacggt gcaggacctg gagagcagga   1860

aagggaaaca gacgcgacag caacaagagc accagaagta tatggtccca ctgcaggcct   1920

cagcacaaga gaagaatgga ctctgaggac tgagaagggg ccttacagaa ccctaaaggg   1980

agggaaggtc ctacaggtct ccggccaccc acacaaggag gaggaagagg aaatggtgac   2040

ccaagtgtgg gggttgtggt tcaggaaagc atcttcccag ggtccacct cccctttataa   2100

accccaccag aaccacatca ttaaaaggtt tgactgcgca ccaaaaaaaa aaaaaaaaaa   2160

aaaaaaaaaa aaaaaaaaaa                                               2180
```

```
<210> SEQ ID NO 14
<211> LENGTH: 2175
<212> TYPE: DNA
<213> ORGANISM: Homo sapiens

<400> SEQUENCE: 14

aaacacagct tgttagagct gagctgccct actacagcag ctgccggccc ctaggacaga     60
```

-continued

```
gcagggacct caactacact gatcaccagc cccatcggat ccagacccgg ccaccagtgc    120
catgaccttc tcggagatcc tggaccgtgt gggaagcatg ggccatttcc agttcctgca    180
tgtagccata ctgggcctcc cgatcctcaa catggccaac cacaacctgc tgcagatctt    240
cacagccgcc acccctgtcc accactgtcg cccgccccac aatgcctcca cagggccttg    300
ggtgctcccc atgggcccaa atgggaagcc tgagaggtgc ctccgttttg tacatccgcc    360
caatgccagc ctgcccaatg acacccagag ggccatggag ccatgcctgg atggctgggt    420
ctacaacagc accaaggact ccattgtgac agagtgggac ttggtgtgca actccaacaa    480
actgaaggag atggcccagt ctatcttcat ggcaggtata ctgattggag ggctcgtgct    540
tggagacctg tctgacaggt ttggccgcag gcccatcctg acctgcagct acctgctgct    600
ggcagccagc ggctccggtg cagccttcag ccccaccttc cccatctaca tggtcttccg    660
cttcctgtgt ggctttggca tctcaggcat taccctgagc accgtcatct tgaatgtgga    720
atgggtgcct acccggatgc gggccatcat gtcgacagca ctcgggtact gctacacctt    780
tggccagttc attctgcccg gcctggccta cgccatcccc cagtggcgtt ggctgcagtt    840
aactgtgtcc attcccttct tcgtcttctt cctatcatcc tggtggacac cagagtccat    900
acgctggttg gtcttgtctg gaaagtcctc gaaggccctg aagatactcc ggcgggtggc    960
tgtcttcaat ggcaagaagg aagagggaga aaggctcagc ttggaggagc tcaaactcaa   1020
cctgcagaag gagatctcct tggccaaggc caagtacacc gcaagtgacc tgttccggat   1080
acccatgctg cgccgcatga ccttctgtct ttccctggcc tggtttgcta ccggttttgc   1140
ctactatagt ttggctatgg gtgtggaaga atttggagtc aacctctaca tcctccagat   1200
catctttggt ggggtcgatg tcccagccaa gttcatcacc atcctctcct taagctacct   1260
gggccggcat accactcagg ccgctgccct gctcctggca ggaggggcca tcttggctct   1320
cacctttgtg cccttggact tgcagaccgt gaggacagta ttggctgtgt ttgggaaggg   1380
atgcctatcc agctccttca gctgcctctt cctctacaca agtgaattat accccacagt   1440
catcaggcaa acaggtatgg gcgtaagtaa cctgtggacc cgcgtgggaa gcatggtgtc   1500
cccgctggtg aaaatcacgg gtgaggtaca gcccttcatc cccaatatca tctacgggat   1560
caccgccctc ctcgggggca gtgctgccct cttcctgcct gagaccctga atcagccctt   1620
gccagagact atcgaagacc tggaaaactg gtccctgcgg gcaaagaagc caaagcagga   1680
gccagaggtg gaaaaggcct cccagaggat ccctctacag cctcacggac caggcctggg   1740
ctccagctga ggacaacgga accccctttc cctgccctcc agagactgat cctagccagg   1800
caccttagga gtatagggag gccccatata ggtccatcct cctaggatga agccttctga   1860
gagcttggtg aaggtgtctc catcaccacc accagagcct cctgcccagc cctggccagt   1920
tcaaaggttc agccatccct gcccttgttc tccctgcaac ccaggccctg ccattcttct   1980
gtctagccct tccccactgg ccaccttccc ccactgtccc ggtcctcttc ccctgaggtc   2040
ccctgatatc ccctggctca gtcctaacaa gactgagtct taacaagatg agaagtcctc   2100
cccttcttgc ctcccacact tttctttgat gggaggtttc aataaacagc gataagaact   2160
ctaaaaaaaa aaaaa                                                    2175
```

<210> SEQ ID NO 15
<211> LENGTH: 1921
<212> TYPE: DNA
<213> ORGANISM: Homo sapiens

<400> SEQUENCE: 15

-continued

```
ctgatttcaa accactcctt ttcaaagatc tctgagggag acattgcacc tggccactgc     60

agcccagagc aggtctggcc acggccatga gcatgctgag ccatcatgcc caccgtggat    120

gacattctgg agcaggttgg ggagtctggc tggttccaga agcaagcctt cctcatctta    180

tgcctgctgt cggctgcctt tgcgcccatc tgtgtgggca tcgtcttcct gggtttcaca    240

cctgaccacc actgccagag tcctggggtg gctgagctga gccagcgctg tggctggagc    300

cctgcggagg agctgaacta tacagtgcca ggcctggggc ccgcgggcga ggccttcctt    360

ggccagtgca ggcgctatga agtggactgg aaccagagcg ccctcagctg tgtagacccc    420

ctggctagcc tggccaccaa caggagccac ctgccgctgg gtccctgcca ggatggctgg    480

gtgtatgaca cgcccggctc ttccatcgtc actgagttca acctggtgtg tgctgactcc    540

tggaagctgg acctctttca gtcctgtttg aatgcgggct tcttgtttgg ctctctcggt    600

gttggctact ttgcagacag gtttggccgt aagctgtgtc tcctgggaac tgtgctggtc    660

aacgcggtgt cgggcgtgct catggccttc tcgcccaact acatgtccat gctgctcttc    720

cgcctgctgc agggcctggt cagcaagggc aactggatgg ctggctacac cctaatcaca    780

gaatttgttg gctcgggctc cagaagaacg gtggcgatca tgtaccagat ggccttcacg    840

gtggggctgg tggcgcttac cgggctggcc tacgccctgc ctcactggcg ctggctgcag    900

ctggcagtct ccctgcccac cttcctcttc ctgctctact actggtgtgt gccggagtcc    960

cctcggtggc tgttatcaca aaaaagaaac actgaagcaa taaagataat ggaccacatc   1020

gctcaaaaga atgggaagtt gcctcctgct gatttaaaga tgctttccct cgaagaggat   1080

gtcaccgaaa agctgagccc ttcatttgca gacctgttcc gcacgccgcg cctgaggaag   1140

cgcaccttca tcctgatgta cctgtggttc acggactctg tgctctatca ggggctcatc   1200

ctgcacatgg gcgccaccag cgggaacctc tacctggatt tcctttactc cgctctggtc   1260

gaaatcccgg gggccttcat agccctcatc accattgacc gcgtgggccg catctacccc   1320

atggccatgt caaatttgtt ggcgggggca gcctgcctcg tcatgatttt tatctcacct   1380

gacctgcact ggttaaacat cataatcatg tgtgttggcc gaatgggaat caccattgca   1440

atacaaatga tctgcctggt gaatgctgag ctgtacccca cattcgtcag gaacctcgga   1500

gtgatggtgt gttcctccct gtgtgacata ggtgggataa tcacccccct catagtcttc   1560

aggctgaggg aggtctggca agccttgccc ctcattttgt ttgcggtgtt gggcctgctt   1620

gccgcgggag tgacgctact tcttccagag accaaggggg tcgctttgcc agagaccatg   1680

aaggacgccg agaaccttgg gagaaaagca aagcccaaag aaaacacgat ttaccttaag   1740

gtccaaacct cagaaccctc gggcacctga gagagatgtt ttgcggcgat gtcgtgttgg   1800

agggatgaag atggagttat cctctgcaga aattcctaga cgccttcact tctctgtatt   1860

cttcctcata cttgcctacc cccaaattaa tatcagtcct aaagaaaaaa aaaaaaaaaa   1920

a                                                                   1921
```

<210> SEQ ID NO 16
<211> LENGTH: 1131
<212> TYPE: DNA
<213> ORGANISM: human herpesvirus 1

<400> SEQUENCE: 16

```
atggcttcgt acccctgcca tcaacacgcg tctgcgttcg accaggctgc gcgttctcgc     60

ggccatagca accgacgtac ggcgttgcgc cctcgccggc agcaagaagc cacggaagtc    120
```

-continued

| | |
|---|---|
| cgcctggagc agaaaatgcc cacgctactg cgggtttata tagacggtcc tcacgggatg | 180 |
| gggaaaacca ccaccacgca actgctggtg gccctgggtt cgcgcgacga tatcgtctac | 240 |
| gtacccgagc cgatgactta ctggcaggtg ctgggggctt ccgagacaat cgcgaacatc | 300 |
| tacaccacac aacaccgcct cgaccagggt gagatatcgg ccggggacgc ggcggtggta | 360 |
| atgacaagcg cccagataac aatgggcatg ccttatgccg tgaccgacgc cgttctggct | 420 |
| cctcatgtcg ggggggaggc tgggagttca catgccccgc ccccggccct caccctcatc | 480 |
| ttcgaccgcc atcccatcgc cgccctcctg tgctacccgg ccgcgcgata ccttatgggc | 540 |
| agcatgaccc cccaggccgt gctggcgttc gtggccctca tcccgccgac cttgcccggc | 600 |
| acaaacatcg tgttgggggc ccttccggag gacagacaca tcgaccgcct ggccaaacgc | 660 |
| cagcgccccg gcgagcggct tgacctggct atgctggccg cgattcgccg cgtttacggg | 720 |
| ctgcttgcca atacggtgcg gtatctgcag ggcggcgggt cgtggtggga ggattgggga | 780 |
| cagctttcgg ggacggccgt gccgccccag ggtgccgagc cccagagcaa cgcgggccca | 840 |
| cgaccccata tcggggacac gttatttacc ctgtttcggg cccccgagtt gctggccccc | 900 |
| aacggcgacc tgtataacgt gtttgcctgg gccttggacg tcttggccaa acgcctccgt | 960 |
| cccatgcacg tctttatcct ggattacgac caatcgcccg ccggctgccg ggacgccctg | 1020 |
| ctgcaactta cctccgggat ggtccagacc cacgtcacca ccccaggctc cataccgacg | 1080 |
| atctgcgacc tggcgcgcac gtttgcccgg gagatggggg aggctaactg a | 1131 |